United States Patent
Chornet Serrano et al.

(10) Patent No.: US 9,909,085 B2
(45) Date of Patent: Mar. 6, 2018

(54) INSTALLATION AND METHOD FOR PRODUCING FATTY ACID ESTERS USABLE AS FUEL

(71) Applicant: SUPERCRITICAL IDEAS, SL, Barcelona (ES)

(72) Inventors: Maria Úrsula Chornet Serrano, Valencia (ES); Pau Azkarate Capell, Barcelona (ES)

(73) Assignee: SUPERCRITICAL IDEAS, SL, Barcelona (ES)

(*) Notice: Subject to any disclaimer, the term of this patent is extended or adjusted under 35 U.S.C. 154(b) by 0 days.

(21) Appl. No.: 15/081,876

(22) Filed: Mar. 26, 2016

(65) Prior Publication Data
US 2016/0264911 A1    Sep. 15, 2016

Related U.S. Application Data

(63) Continuation of application No. PCT/IB2014/001976, filed on Oct. 1, 2014.

(51) Int. Cl.
*C11C 3/10* (2006.01)
*C11C 3/04* (2006.01)
(Continued)

(52) U.S. Cl.
CPC ............. *C11C 3/10* (2013.01); *B01J 19/0066* (2013.01); *B01J 19/1812* (2013.01);
(Continued)

(58) Field of Classification Search
CPC ... C11C 3/04; C11C 3/10; C11C 3/003; C07C 67/02; C07C 67/03; C07C 67/08; B01J 19/1812; B01J 19/1825; B01J 19/1856
See application file for complete search history.

(56) References Cited

U.S. PATENT DOCUMENTS 6,187,939 B1    2/2001  Sasaki et al.
2003/0065202 A1  4/2003  Goto et al.
(Continued)

FOREIGN PATENT DOCUMENTS

JP    2004182966 A    7/2004
JP    2006 188590 A   7/2006
(Continued)

OTHER PUBLICATIONS

Taniguchi Katsuhiro, et al, JP 2004-182966, Manufacturing Plant for Fatty Acid Ester, 2004, pp. 1-17 (English translation).*

Primary Examiner — Yate' K Cutliff
(74) Attorney, Agent, or Firm — Robert J. Hess; Hess Patent Law Firm

(57) ABSTRACT

Installation and method for producing fatty acid esters usable as fuel for which the installation includes a tank (10) containing oils and/or fats to be treated, a tank (11) containing light alcohol, pumps (3) and (4) feeding the materials to a tubular reaction vessel (30) having a winding configuration provided with a heater for internally maintaining a supercritical temperature with respect to the alcohol used and a pressure provided by the pumps, suitable for producing esterification and transesterification reactions, without the presence of catalysts of the oils and/or fats and alcohol, a heat exchanger (8) for heating the affluents and cooling the reaction effluents and a reaction effluent depressurization tank (21). The installation further has a stirrer (22, 23, 28) for stirring the reaction product at the reaction temperature and pressure in one or more segments of the tubular vessel (30) covering a sector of the reactor before its end area for exit towards the depressurization tank (21).

5 Claims, 5 Drawing Sheets

(51) Int. Cl.
  *C07C 67/02* (2006.01)
  *C07C 67/08* (2006.01)
  *C11C 3/00* (2006.01)
  *B01J 19/00* (2006.01)
  *B01J 19/18* (2006.01)
  *C10L 1/02* (2006.01)
  C07C 67/03 (2006.01)

(52) U.S. Cl.
  CPC .............. *C07C 67/02* (2013.01); *C07C 67/08* (2013.01); *C10L 1/026* (2013.01); *C11C 3/003* (2013.01); *C11C 3/04* (2013.01); *B01J 2219/0009* (2013.01); B01J 2219/00103 (2013.01); C07C 67/03 (2013.01); C10L 2200/0476 (2013.01); C10L 2270/026 (2013.01); C10L 2290/06 (2013.01); C10L 2290/24 (2013.01); Y02E 50/13 (2013.01)

(56) References Cited

U.S. PATENT DOCUMENTS

| | | |
|---|---|---|
| 2006/0025620 A1 | 2/2006 | Saka |
| 2009/0264671 A1 | 10/2009 | Noh et al. |
| 2009/0277077 A1 | 11/2009 | Gleason et al. |
| 2011/0271585 A1 | 11/2011 | Miller |

FOREIGN PATENT DOCUMENTS

| | | |
|---|---|---|
| JP | 2006 036817 A | 2/2009 |
| WO | WO 2015/049573 | 4/2015 |

* cited by examiner

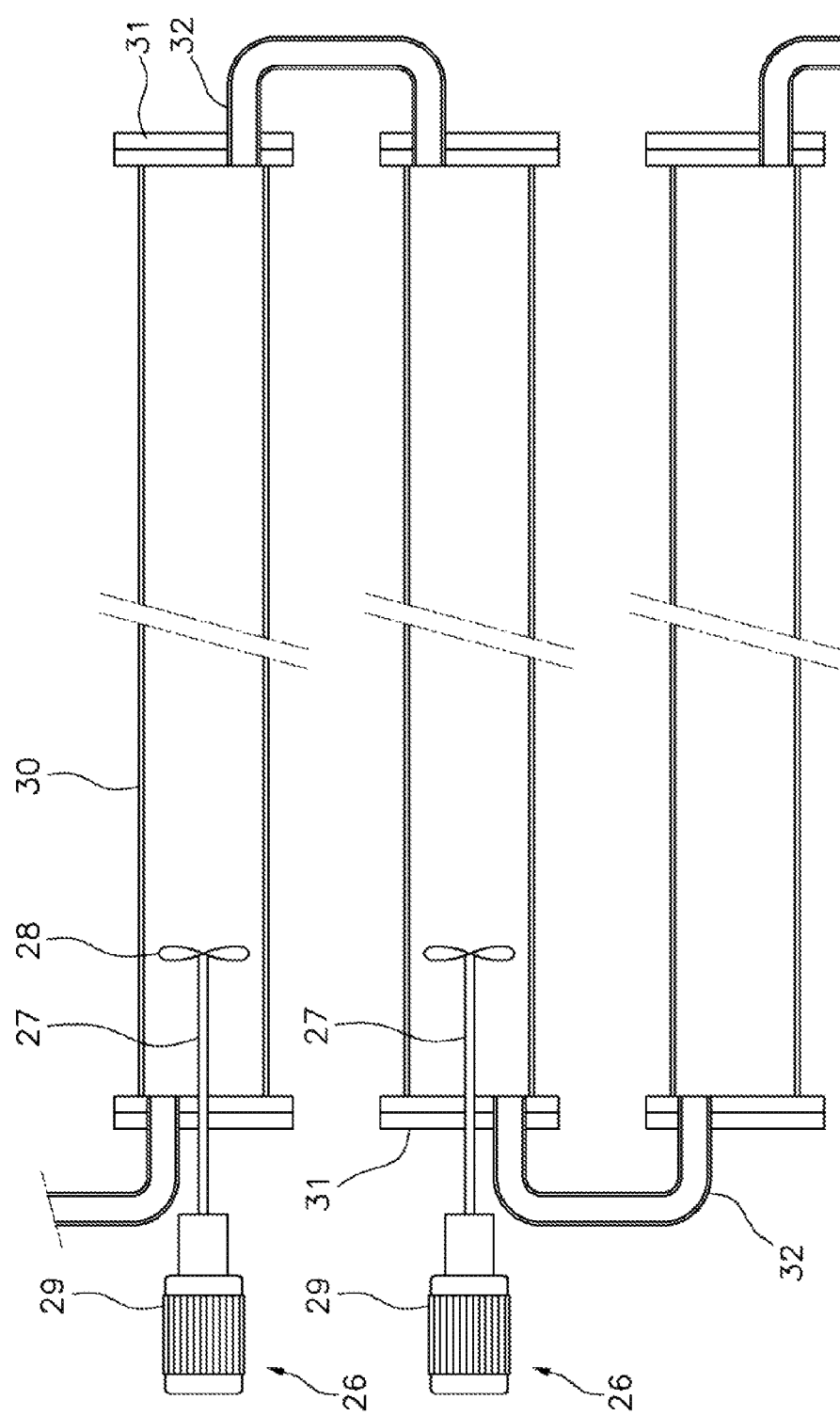

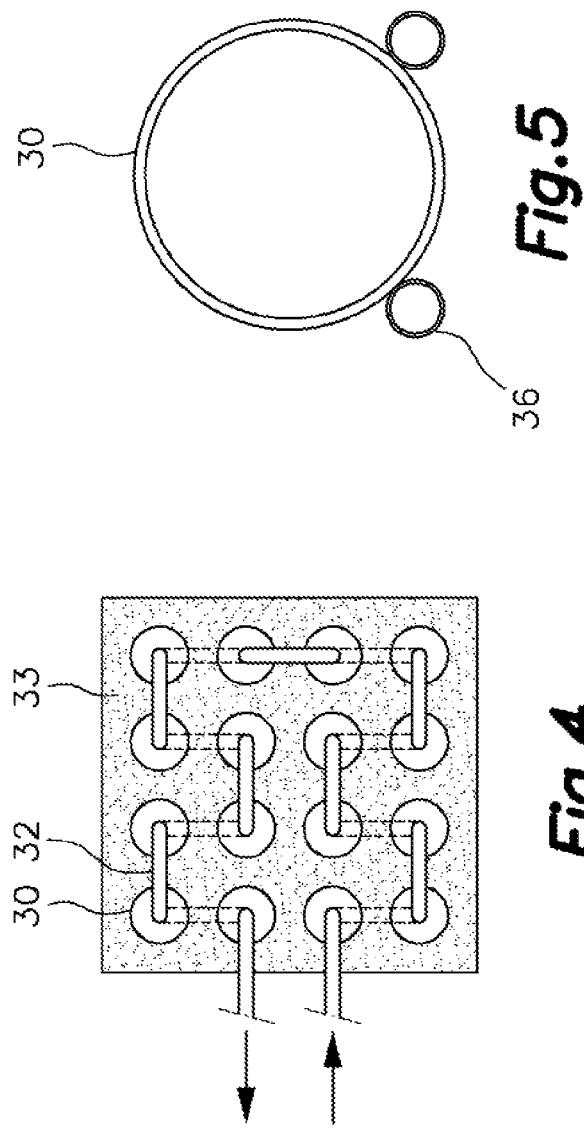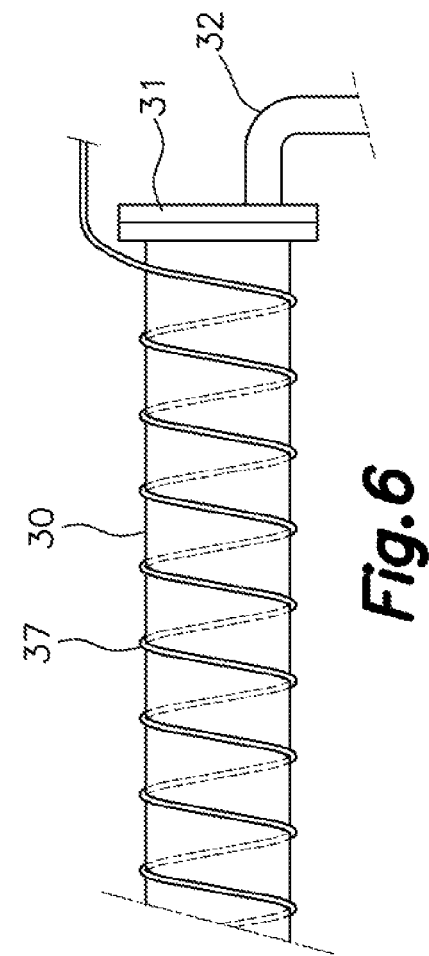

INSTALLATION AND METHOD FOR PRODUCING FATTY ACID ESTERS USABLE AS FUEL

FIELD OF THE INVENTION

The present invention relates to an installation for producing fatty acid esters from oils and/or fats and at least one alcohol such as methanol.

The invention also relates to a method for producing said fatty acid esters.

The invention is applicable for biodiesel preparation, in the cases in which the starting material (oils and/or fats) is of a plant or animal origin; however, in addition to the use as fuel the obtained fatty acid esters are usable for various applications in the chemical and cosmetic industry.

BACKGROUND OF THE INVENTION

Biodiesel has become quite important among biofuels, there being a growing trend in constructing industrial plants for producing biodiesel based primarily on esterification and transesterification reactions of said oils and/or fats and alcohol without the presence of catalysts, wherein the reaction takes place at a high pressure and temperature, an alcohol which facilitates breaking the bond linking glycerin with fatty acids and allows the formation of glycerol on one hand and esters on the other, being required.

Document JP 2004182966 discloses an installation for producing fatty acid esters from mixtures of fats and oils in a tubular reactor operating in supercritical state. The installation comprises a preheater for preheating the oil and fats fed to the reactor, a preheater for preheating the alcohol at a temperature lower than the critical temperature of said alcohol and equipment for raising the temperature of a mixture of said preheated oil and fat and said preheated alcohol to the reaction temperature before feeding to the reactor. This document discloses also the integration of a stirring device placed previous to the reactor producing a mixing of the alcohol with the fats and oils.

Documents JP2006188590 and JP2006036817 have the same inventor than the preceding document cited and disclose the same installation including minor differences not relevant for the present invention. Both additional documents integrate said stirring device in a position previous to the reactor.

Document US2006025620 discloses a method for producing a esterification reaction where examples 1 and 4 exposes a method produced in a laboratory scale, using small batch type apparatus, eg. a reaction tube. This reaction tube was placed into a tin bath controlled at a predetermined temperature and reacted while shaking under a predetermined pressure for a predetermined time, but this document do not disclose a reaction method produced in a flow type apparatus including said shaking of the product while the reaction is performed, and do not exposes means for shaking or stirring included in a flow type reactor. International patent application WO 2007/026032 discloses a chemical reactor for supercritical alcoholysis of all types of fats and oils with various alcohols wherein both the fats and the oils are introduced directly into the reactor by respective pumps, heat exchangers for the effluents and for the fats and oils fed to the chemical reactor having been envisaged.

The invention proposes a reactor such as that described in the preceding documents in which the reaction conditions have been improved, facilitating the conversion of fatty acids treated by means of applying several measures that do not exist in said prior art.

DISCLOSURE OF THE INVENTION

According to the art which is known and already disclosed by the aforementioned documents, the proposed tubular reactor comprises:

a first tank containing oils and/or fats to be treated connected by a supply pipe to a first pump for feeding said oils and/or fats at a predetermined pressure suitable for the described reaction process to be performed under supercritical conditions;

a second tank containing a light alcohol connected by a supply pipe to a second pump for feeding said alcohol at said same predetermined pressure;

a reactor to which said first and second pumps feed said oils and/or fats and alcohol, and comprising a tubular reaction vessel with a winding or coil configuration having a considerable length to allow for the reaction time, which is about 30 to 45 minutes or even greater; the mentioned coil has heating means associated therewith suitable for internally maintaining a supercritical temperature (in the order of 280° C. to 325° C.) in relation to the alcohol used and a pressure of between 15 and 25 Mpa, provided by said first and second pumps, suitable for producing esterification and transesterification reactions of said oils and/or fats and alcohol without the presence of catalysts;

heat exchangers for heating the affluents which comprises, in the present proposal, the fats and oils and alcohol, and cooling the effluents or products resulting from the reaction;

a third reaction effluent depressurization tank equipped with pressure/flow rate regulating valves for depressurization, connected to an end area of the reactor for the exit of the reaction effluents; and means for recovering the excess alcohol of the reaction which are associated with said depressurization tank, having an outlet for the produced esters and reaction by-products which are subsequently separated.

According to the proposal of this invention, the installation further comprises means for stirring the reaction product in one or more segments of the tubular vessel covering a sector thereof (longer or shorter in length, as appropriate) before its end area for exit towards the depressurization tank.

In a first embodiment, the stirring means comprise at least one third pump recirculating the reaction product at the reaction pressure through a recirculation pipe with an inlet in an area of the vessel close to said end area of the reactor (which as indicated is connected to the depressurization tank) and an outlet in a front area of the tubular vessel whereby an increase in reaction product speed is generated in a sector of the tubular vessel demarcated by said inlet and outlet of the recirculation pipe and covering a segment of the reactor before its end area. It has been verified that said speed increase in a final segment of the reactor favors the reaction in said end area as it causes the stirring of the reaction product cooperating to a greater extent with said reaction.

By means of such arrangement, the movement or oscillations of the reaction product are achieved and performing said reaction is favored mainly at the end area of the reactor where said reaction has been observed to be slower and can even be incomplete.

Alternatively, said stirring can be performed by means of applying one or more stirrer devices comprising a propeller at the end of a rod operated by a motor, said propeller and part of the rod being arranged inside the reactor and rotary gasket means coaxial to a portion of the rod having been envisaged.

The invention further proposes providing the fats and the oils together with the alcohol directly to the reactor and a mixer device, such as a static mixer (even though it could also be a dynamic mixer, using a stirrer device such as the mentioned stirrer for stirring the reaction product) has been envisaged for that purpose, to which mixer device the pressurized fluids fed by said first and second pumps are channeled. The reaction mixture is transported countercurrent from said mixer by a first pipe to a first heat exchanger which provides said fluids with thermal energy from the reaction effluents, and returned through a second pipe carrying said heated reaction mixture to a second heat exchanger which provides it with thermal energy before introducing said mixture at the reaction temperature into the reactor.

Reaction initiation inside the reactor from the start thereof is thus facilitated with respect to the proposals described in the mentioned prior art.

To assure the development of the reaction, it has also been envisaged to control and correct, if necessary, the temperature deviations in different segments throughout the reactor by providing means for taking temperature and for providing thermal energy that will be described in detail in reference to the attached drawings and according to several embodiments.

It has also been envisaged that for treating specific oils, for example palmitic acid, in addition to the mentioned reactor, a second tubular reactor having a similar structure, intercalated before the depressurization tank, is used, in which a heterogeneous catalyzed treatment step is performed at a subcritical temperature of about 150° C. and at a pressure in the order of 2 Mpa.

As indicated, the invention also proposes a method for producing fatty acid esters usable as fuel from oils and/or fats and at least one alcohol which comprises performing esterification and transesterification reactions of a mixture of said oils and/or fats and alcohol inside a reactor made up of a tubular vessel having a winding or coil configuration at a pressure comprised between 15 and 25 Mpa and at a supercritical temperature in relation to the alcohol used of between 280° C. and 325° C., for about 30 to 45 minutes, and recovering the esters in a depressurization tank to which an outlet of the mentioned reactor is connected, where said stirring of the reaction mixture in an area of the reactor close to its outlet has further been envisaged.

It has further been envisaged that an additional heterogeneous catalyzed treatment which is performed in a second reactor in which the reaction will occur at a subcritical temperature of about 150° C. and at a pressure of 2 Mpa for one or two hours, is applied for specific oils and/or fats (for example, palmitic acid).

The invention will be described below basically in reference to the proposed installation with the aid of several illustrative and non-limiting schematic drawings.

BRIEF DESCRIPTION OF THE DRAWINGS

FIG. 3 illustrates a possible construction of the tubular reactor of the invention, including means for stirring the product alternative to those of said first example.

FIG. 4 shows schematic elevational view of a possible embodiment of a reactor such as that described, comprising 16 linear segments interconnected by connection elbows and surrounded by heat insulating material.

FIG. 5 shows a second embodiment alternative to that of FIG. 2 for maintaining the temperature of the segments of the tubular reactor.

FIG. 6 illustrates a third embodiment alternative to that of FIG. 2 for maintaining the temperature of the segments of the tubular reactor.

Finally.

DETAILED DESCRIPTION OF EMBODIMENTS

Figure 1:
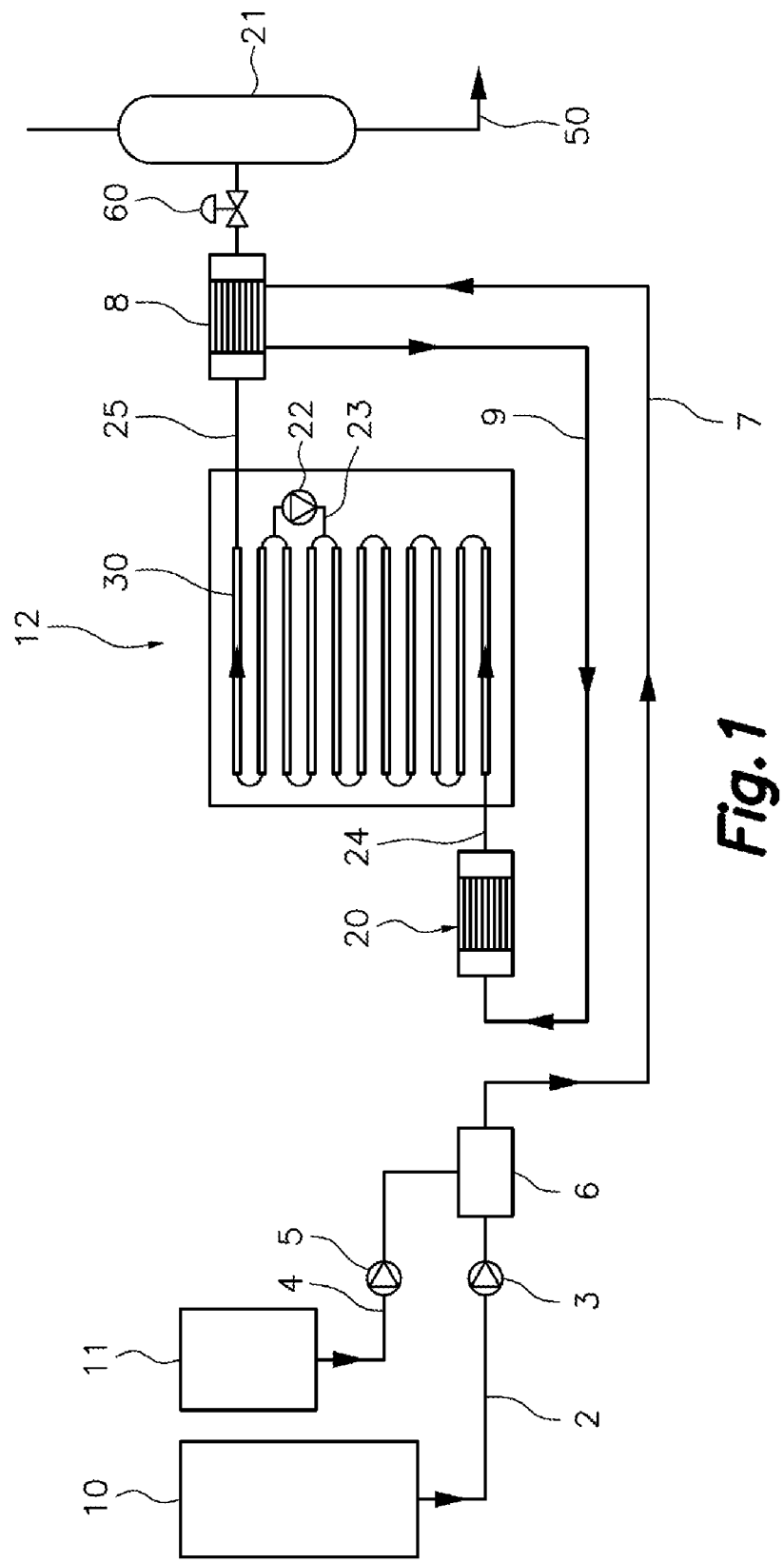
FIG. 1 shows the installation as a whole indicating the improvement details implemented according to a first embodiment.

As shown in FIG. 1, according to the structure which is already known in the state of the art the proposed installation for producing fatty esters comprises:

- a first tank 10 containing oils and/or fats to be treated connected by a supply pipe 2 to a first pump for feeding said oils or fats at a predetermined pressure;
- a second tank 11 containing a light alcohol connected by a supply pipe 4 to a second pump 5 for feeding said alcohol at said same predetermined pressure;
- a reactor 12 to which said first and second pumps 3, 5 feed said oils and/or fats and alcohol under pressure, and comprising a tubular reaction vessel with a winding or coil configuration having heating means associated therewith suitable for internally maintaining a supercritical temperature in relation to the alcohol used and a pressure, provided by said first and second pumps 3, 5, suitable for producing esterification and transesterification reactions of said oils and/or fats and alcohol without the presence of catalysts;
- a heat exchanger 8 for heating the affluents and cooling the reaction effluents;
- a reaction effluent depressurization tank 21 equipped with pressure/flow rate regulating valves 60 for depressurization, connected to an end area of the reactor for the exit of the reaction effluents; and
- means for recovering the excess alcohol of the reaction which are associated with said depressurization tank 21 having an outlet 50 for the produced esters and reaction by-products which are subsequently separated by conventional means.

According to the proposal of this invention, means for stirring the reaction product at the reaction temperature and pressure in one or more segments of the tubular vessel 30 covering a sector of the reactor before its end area for exit towards the mentioned depressurization tank have been envisaged in said reactor.

Figure 2:
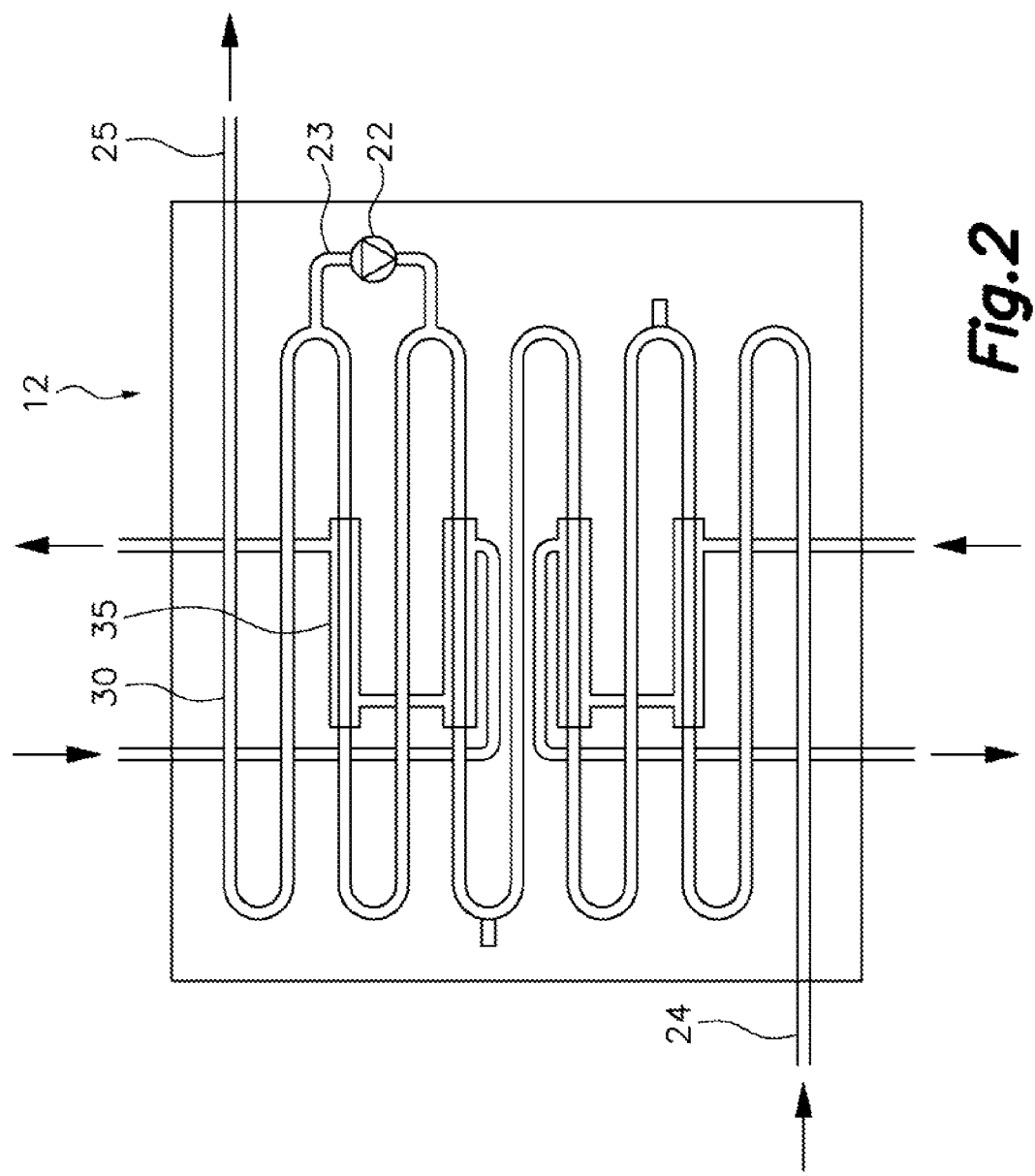
FIG. 2 is an enlarged view of the tubular reactor of said first example indicating means for providing energy to the various segments of the reactor and controlling the temperature inside said segments.

In a first embodiment illustrated in FIGS. 1 and 2, said means for stirring the reaction product comprise a third pump 22 recirculating the reaction product at the reaction pressure through a recirculation pipe 23 with an inlet in an area of the vessel close to said end area of the reactor and an outlet in a front area of the tubular vessel whereby an increase in reaction product speed and a movement thereof are generated in a sector of the tubular vessel demarcated by said inlet and outlet of the recirculation pipe 23 and covering said sector of the reactor before its end area.

Figure 7:
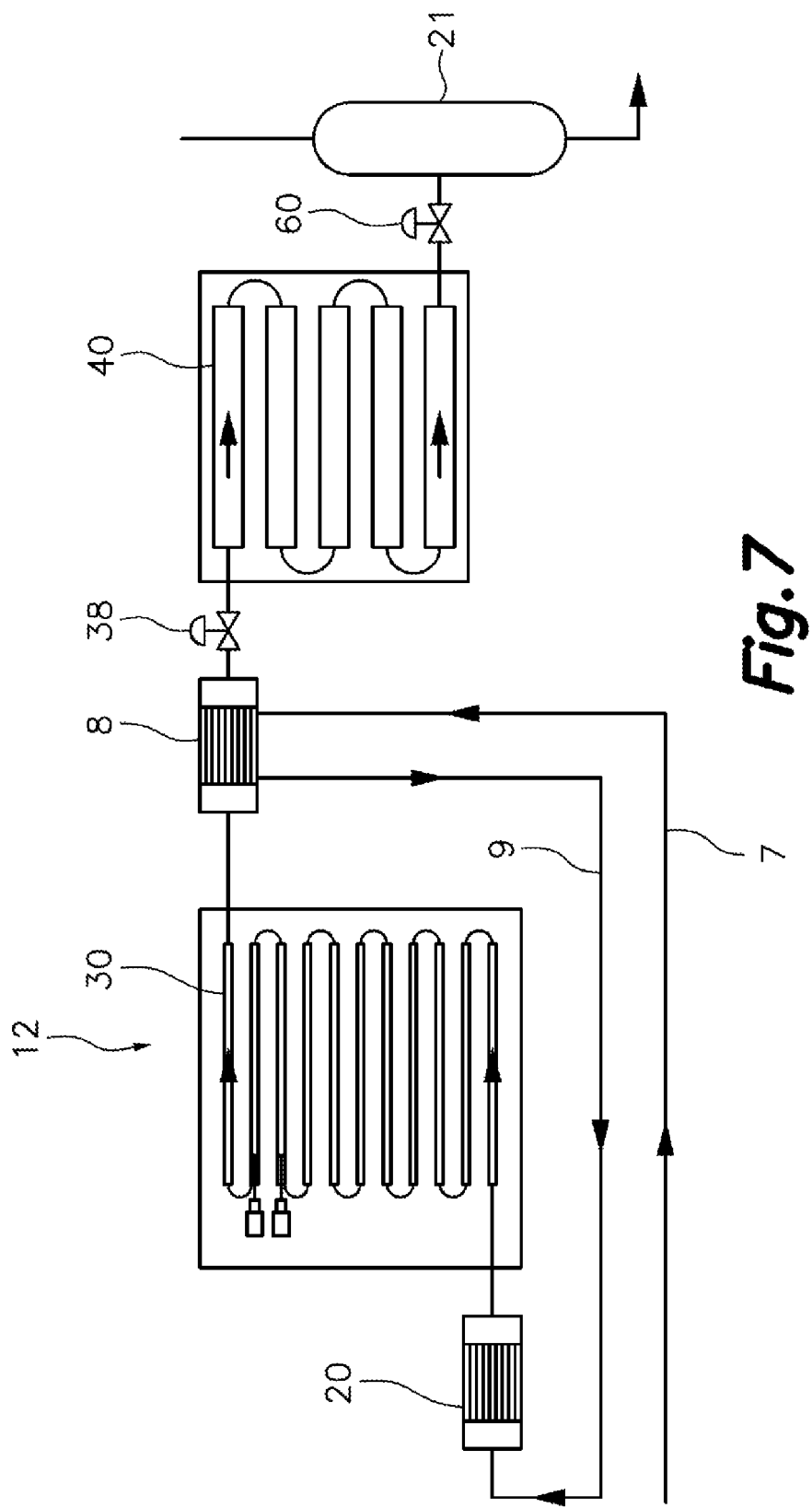
FIG. 7 illustrates an installation where in addition to the described tubular reactor, a second reactor is used in which an additional heterogeneously catalyzed step necessary for treating certain oils is performed.

In a second embodiment illustrated in FIGS. 3 and 7, said means for stirring the reaction product comprise a stirrer device 26 with a propeller 28 at the end of a rod 27 operated by a motor 29, said propeller 28 and part of the rod 27 being inserted into the tubular vessel with a gasket coaxial to the rod 27. In this example, at least two stirrer devices have been envisaged located in segments of the tubular vessel before the outlet of the reactor.

As shown in this FIG. 1, the installation according to a preferred embodiment also includes
- a first mixer device 6 (static or dynamic mixer) to which the pressurized fluids fed by said first and second pumps 3, 5 are channeled;
- a first pipe 7 transporting the reaction mixture countercurrent from said mixer device 6 to a first heat exchanger 8 which provides said fluids with thermal energy from the reaction effluents, and
- a second pipe 9 transporting said heated reaction mixture from the mentioned first heat exchanger 8 to a second heat exchanger 20 which provides it with thermal energy before introducing said mixture at the reaction temperature into the reactor.

In order to assure that the pressurized fluids enter the reactor 12 in a suitably mixed state, the arrangement of a stirrer device (not depicted in the drawing), for example a stirrer with blades or a propeller operated by a motor, after said second heat exchanger 20 and in the reaction mixture feed pipe 24 is proposed.

As can be seen in FIG. 3, a possible construction of the tubular vessel 30 is made by means of a plurality of linear segments of a first section which are closed at each of the ends thereof by a plate 31 and interconnected by connection elbows 32 of a second smaller section going through said plate, the stirrer device 26 being seen to be installed linked to said end plate 31, along with said connection elbows 32, and its rod 27 passes into the tubular vessel through a hole of said plate 31.

If said third pump 22 is used as a stirrer device, said third pump 22 will be intercalated in the mentioned recirculation pipe linking two of the connection elbows 32.

FIG. 4 shows a possible construction of a tubular reactor by means of a plurality of linear segments 30 linked by connection elbows 32. The assembly of said tubular segments 30 supported in a support structure (not seen in the drawing) are surrounded by a heat insulating material, for example glass wool 33, by way of an enveloping block.

FIG. 2 shows in detail means for providing thermal energy to one or more of said segments of the tubular vessel 30 of the reactor in order to keep the temperature throughout the tubular vessel under control and said means comprise tubular sleeves 35 enveloping several of the segments of the tubular vessel 30 in which devices for measuring the temperature are arranged, said tubular sleeves 35 being associated with means for selectively feeding a controlled-temperature fluid into said sleeves to provide a specific thermal energy, if necessary, and to assure that the temperature in the tubular vessel of the reactor is maintained within the indicated range of 280° C. and 325° C.

The mentioned sleeves 35 can be individually fed with said controlled-temperature fluid or two or more of said sleeves 35 enveloping specific segments of the tubular vessel are interconnected to one another and jointly fed with a controlled-temperature fluid.

FIG. 5 illustrates an alternative embodiment of said means for providing thermal energy to the segments of the tubular vessel 30 made up of complementary or tracer pipes 36 in thermal contact with said tubes of the tubular reactor.

FIG. 6 shows another possible embodiment of said means for providing thermal energy made up by means of a heater element in the form of a tracer wire 37 with a flameproof envelopment.

FIG. 7 shows an additional aspect of the invention, where it has been envisaged that said reactor 12 has, associated with its outlet and communicated by a control valve 38, intercalated with the depressurization tank 21, a second tubular reaction vessel 40 with a winding or coil configuration and provided with heating means for heating to a subcritical temperature of about 150° C., providing a treatment step, in this case a heterogeneous catalyzed treatment step, for treating specific oils and/or fats at a pressure in the order of 2 Mpa.

What is claimed is:

1. A method for producing fatty acid esters usable as fuel from oils and/or fats and at least one alcohol which comprises performing esterification and transesterification reactions of a mixture of said oils and/or fats and alcohol inside a reactor made up of a tubular vessel which has a winding or coil configuration and operates at a pressure comprised between 15 and 25 Mpa and at a supercritical temperature in relation to the alcohol used of between 280° C. and 325° C. and recovering the esters resulting from the reaction in a depressurization tank to which an outlet of the mentioned reactor is connected, wherein the reaction mixture inside the reactor operating under said pressure and temperature conditions of the reactor is stirred in a sector of the tubular vessel covering one or more segments of the reactor (12) before its end area which is connected to the depressurization tank to favor the reaction mainly at the end area of the reactor close to said outlet.

2. The method according to claim 1, wherein said reaction inside the reactor (12) lasts for 30 to 45 minutes.

3. The method according to claim 1, characterized by comprising an additional heterogeneous catalyzed treatment step which is performed in a second tubular reaction vessel (40) at a subcritical temperature of about 150° C. and at a pressure in the order of 2 Mpa.

4. The method according to claim 1, wherein said stirring is produced by means of a pump recirculating the reaction product at the reaction pressure through a recirculation pipe.

5. The method according to claim 1, wherein said stirring is produced by means of one or more stirrer devices comprising a propeller at the end of a rod operated by a motor.

* * * * *